(12) United States Patent  
Kurokawa (10) Patent No.: US 8,641,629 B2  
(45) Date of Patent: Feb. 4, 2014

(54) ULTRASONIC PROBE, CHARGER, ULTRASONIC DIAGNOSTIC APPARATUS AND ULTRASONIC DIAGNOSTIC SYSTEM

(75) Inventor: Shinya Kurokawa, Kanagawa (JP)

(73) Assignee: Panasonic Corporation, Osaka (JP)

( * ) Notice: Subject to any disclaimer, the term of this patent is extended or adjusted under 35 U.S.C. 154(b) by 584 days.

(21) Appl. No.: 12/250,905

(22) Filed: Oct. 14, 2008

(65) Prior Publication Data

US 2009/0112099 A1    Apr. 30, 2009

(30) Foreign Application Priority Data

Oct. 19, 2007    (JP) ................................. 2007-272055

(51) Int. Cl.
*A61B 8/14*        (2006.01)
(52) U.S. Cl.
USPC .......................................... 600/459; 320/108
(58) Field of Classification Search
USPC .................................. 600/459; 320/108, 114
See application file for complete search history.

(56) References Cited

U.S. PATENT DOCUMENTS 6,117,085 A * 9/2000 Picatti et al. .................. 600/459

FOREIGN PATENT DOCUMENTS

| JP | 2000-107176 A | 4/2000 |
|----|---------------|--------|
| JP | 2003-010177 A | 1/2003 |

\* cited by examiner

*Primary Examiner* — Unsu Jung
*Assistant Examiner* — Saurel J Selkin
(74) *Attorney, Agent, or Firm* — Pearne & Gordon LLP (57) ABSTRACT

An ultrasonic probe, a charger and an ultrasonic diagnostic apparatus, and an ultrasonic diagnostic system that uses them are provided by the present invention, which comprises a detector for detecting whether or not an ultrasonic probe having a rechargeable battery or the charger for charging this is in charging state; and a controller for stopping transmitting and receiving operations of ultrasonic waves. The ultrasonic diagnostic apparatus comprises a transmitting and receiving circuit for executing the generation of a signal related to the transmission of the ultrasonic waves and the generation of the diagnostic information based on the signal related to the reception of the ultrasonic waves; a probe switching circuit for selecting one of a plurality of ultrasonic probes; and a controller for controlling the probe switching circuit in accordance with a detection signal from the detector. The ultrasonic diagnostic system comprises the above-mentioned probes, chargers and diagnostic apparatus.

8 Claims, 10 Drawing Sheets

ULTRASONIC PROBE, CHARGER, ULTRASONIC DIAGNOSTIC APPARATUS AND ULTRASONIC DIAGNOSTIC SYSTEM

TECHNICAL FIELD

The present invention relates to a cordless ultrasonic probe that uses a rechargeable battery, a charger for charging this ultrasonic probe, an ultrasonic diagnostic apparatus for switching and using a plurality of ultrasonic probes, and an ultrasonic diagnostic system including them.

BACKGROUND ART

In ultrasonic diagnosis, ultrasonic waves are transmitted into a diagnosis target, and an echo signal thereof is received, thereby obtaining various kinds of diagnostic pieces of information such as the tomogram of the diagnostic target and the like. Although the transmission and reception of the ultrasonic waves were executed through an ultrasonic probe, the conventional ultrasonic probe was configured to be connected through a cable to an ultrasonic diagnostic apparatus (in this specification, an ultrasonic diagnostic apparatus body is referred to as an ultrasonic diagnostic apparatus, and a system that includes the ultrasonic probe and the ultrasonic diagnostic apparatus body is referred to as the ultrasonic diagnostic system).

When the ultrasonic diagnosis is executed, there are the various styles such as a case that a patient lies down on a bed or sits on a chair, and other cases. Among them, even in the case that the patient lies down on the bed, the probe is touched to the patient in the various states depending on the patient's position or diagnostic portion, and the diagnosis is executed. At that time, the number of operators who feel troublesome in setting the cable is not small, and the easiness of setting such as the lightness and softness of the cable is one of the features of the ultrasonic probe.

The following patent document 1 describes an ultrasonic diagnostic system that uses a cordless ultrasonic probe in which an ultrasonic transmitting/receiving unit operated with a secondary battery as an operational power source is built, in order to solve this troublesomeness. According to this ultrasonic diagnostic system, the ultrasonic probe can be operated without any feeling of the troublesomeness when the conventional cable is set around.

Also, the current diagnostic regions based on ultrasonic waves is wide-ranging, and there appears a system in which plural probes are used by switching in accordance with each diagnostic region. In such an ultrasonic diagnostic system, when selecting a probe to be used, there was a necessity that the operator operates a selecting switch mounted on the operational panel of the ultrasonic diagnostic apparatus. Therefore, an operator was required to memorize the relationship between probes to be used and the selecting switch, and in that case, there was also a possibility that an incorrect selecting switch was operated.

The following patent document 2 describes an ultrasonic diagnostic system containing a controller in which among the plurality of probes connected to the ultrasonic diagnostic apparatus, the holding onto a probe holder is identified by a sensor, and the transmission and reception of the ultrasonic waves can be performed on only the probe that is not held. According to this ultrasonic diagnostic system, the probe to be used by the operator is taken out from the probe holder arranged in the ultrasonic diagnostic apparatus. Thus, since the taken-out probe is automatically switched to a usable state, the operability is improved, and the burden on the operator is reduced.

Patent Document 1: Japanese Patent Application Publication 2003-10177 (Abstract)
Patent Document 2: Japanese Patent Application Publication 2000-107176 (Abstract)

DISCLOSURE OF THE INVENTION

However, since the cordless ultrasonic probe described in the patent document 1 operates using the secondary battery as the power source, unless the ultrasonic probe is charged, it cannot be used. For this reason, it can be assumed that there may be a case in which, when the ultrasonic probe is not used for diagnosis, it is connected to the charger. At that time, in the charging state while the ultrasonic waves are transmitted, a part of the charge amount per unit time, which corresponds to the energy required to transmit ultrasonic waves, is consumed. Hence, there was a problem that the battery could not be charged efficiently in a short time.

Also, as described in the patent document 2, in the ultrasonic diagnostic system in which the probe to be used is taken out from a probe holding unit arranged in the ultrasonic diagnostic apparatus and then the taken-out probe is automatically switched to the usable state, there is the necessity that a unit for externally identifying whether or not the probe is held on the probe holding unit arranged in the ultrasonic diagnostic apparatus is separately arranged.

The present invention is intended to solve the problems of the above-mentioned conventional techniques. Therefore, its object is to provide an ultrasonic probe, a charger, an ultrasonic diagnostic apparatus and an ultrasonic diagnostic system, in which the ultrasonic probe connected to the charger can be charged efficiently in a short time.

Another object of the present invention is to provide an ultrasonic diagnostic apparatus and an ultrasonic diagnostic system, with which ultrasonic diagnosis can be started by an operator without knowing as to whether or not the ultrasonic probe is in process of charging, and the improvement of the operability can be consequently attained and the burden on the operator can be reduced.

In order to attain the above-mentioned objects, the present invention provide an ultrasonic probe comprising:
a rechargeable battery;
a transducer that uses said battery as an operational power source and transmits and receives ultrasonic waves;
a communicator that uses said battery as the operational power source and wirelessly communicates with outside using a signal related to the transmission and reception by said transducer;
a detector for detecting that said battery is connected to a charger; and
a controller for stopping transmitting and receiving operations of the ultrasonic waves that are executed by said transducer, when it is detected by said detector that said battery is connected to said charger.

With this configuration, when the ultrasonic probe is connected to the charger, the transmitting and receiving operations of the ultrasonic waves are automatically stopped, thereby suppressing the consumption corresponding to the energy required to transmit the ultrasonic waves. Thus, the charge amount per unit time is increased, and the ultrasonic probe can be charged efficiently in a short time.

Also, the present invention is a charger for charging a battery of an ultrasonic probe that contains a transducer for transmitting and receiving ultrasonic waves using a rechargeable battery as an operational power source, and a communicator for wirelessly communicating with outside using a signal related to the transmission and reception by said transducer, said charger comprising:

a detector for detecting that said ultrasonic probe is connected to said charger to charge said battery; and a controller for stopping the transmitting and receiving operations of ultrasonic waves that are executed by said transducer, when the connection of said ultrasonic probe is detected by said detector.

With this configuration, when the ultrasonic probe is connected to the charger, the transmitting and receiving operations of the ultrasonic waves are automatically stopped, thereby enabling the ultrasonic probe to be charged efficiently in a short time.

Also, the present invention is a charger for charging a battery of an ultrasonic probe that contains a transducer that uses a rechargeable battery as an operational power source and executes transmitting and receiving operations of ultrasonic waves, and a communicator that wirelessly communicates with outside using a signal related to the transmission and reception of said transducer, said charger comprising:

a detector for detecting that said ultrasonic probe is connected to said charger to charge said battery; and a signal transmitter for transmitting a detection signal from said detector to outside.

Since this configuration enables the communication using the signal related to the transmission and reception by the transducer to be shut off from the outside, the ultrasonic probe connected to the charger can be charged efficiently in a short time.

Also, the present invention is an ultrasonic diagnostic apparatus that uses respective rechargeable batteries as operational power sources, and sets, as the target of a communication, a plurality of ultrasonic probes for executing: the transmission and reception of ultrasonic waves to and from an examinee; and the wireless transmission/reception of the signal related to the transmission and a reception of said ultrasonic waves to and from an external apparatus, and selects any one of said plurality of ultrasonic probes, in accordance with the detection signals obtained by detecting that said ultrasonic probes are connected to the chargers for charging said batteries, respectively, and transmits/receives the signal related to the transmission and reception of said ultrasonic waves, and contains:

a communicator for wirelessly communicating the signal related to the transmission and reception of said ultrasonic waves;

a transmitting and receiving circuit for generating the signal related to the transmission of the ultrasonic signal in said ultrasonic probe, and adding as the transmission signal to said ultrasonic probe to said communicator, and generating a diagnostic information on the basis of the signal related to the reception of the ultrasonic waves in said ultrasonic probe that is received in said communicator;

a probe switching circuit for selecting any one of said plurality of ultrasonic probes and enabling the transmission/reception to/from said transmitting and receiving circuit; and a controller for controlling said probe switching circuit so that said ultrasonic probe which is not connected to said charger is selected, in accordance with said detection signal.

With this configuration, when the operator removes the ultrasonic probe used for the diagnosis from the charger, only its ultrasonic probe executes the transmission and reception of the ultrasonic waves, and the ultrasonic probe that is still connected to the charger does not execute the transmission and reception of the ultrasonic waves. Thus, the ultrasonic probe connected to the charger can be charged efficiently in a short time. Also, when the operator removes the ultrasonic probe used for the diagnosis from the charger, its ultrasonic probe is automatically switched to the usable state. Thus, the operator has no necessity of storing the relation between the ultrasonic probe and the selecting switch, and there is no fear that the selecting switch is erroneously operated. Hence, the improvement of the operability can be attained, and the burden on the operator can be decreased.

Also, the present invention is an ultrasonic diagnostic system comprising: a plurality of ultrasonic probes for transmitting and receiving ultrasonic waves, a plurality of chargers for charging said ultrasonic probes respectively and individually, and an ultrasonic diagnostic apparatus for transmitting/receiving a signal to/from said ultrasonic probes to generate diagnostic information, wherein said probe comprises:
a rechargeable battery;
a transducer that uses said battery as an operational power source and transmits and receives ultrasonic waves to and from an examinee; and
a first communicator that uses said battery as an operational power source and wirelessly communicates, using a signal related to the transmission and reception of said transducer, with said ultrasonic diagnostic apparatus,
said charger comprises:
a detector for detecting that said ultrasonic probe is connected; and
a signal transmitter for transmitting a detection signal from said detector to said ultrasonic diagnostic apparatus, and
said ultrasonic diagnostic apparatus comprises:
a communicator for wirelessly communicating by using a signal related to the transmission and reception of said ultrasonic waves;
a transmitting and receiving circuit for generating the signal related to the transmission of the ultrasonic waves by said ultrasonic probe, and supplying to said communicator as a transmission signal to said ultrasonic probe, and generating diagnostic information in accordance with the signal related to the reception of the ultrasonic waves in said ultrasonic probe, which signal is received by said communicator;
a probe switching circuit for selecting any one of said plurality of ultrasonic probes to enable the transmission/reception to/from said transmitting and receiving circuit; and
a controller for controlling said probe switching circuit so that said ultrasonic probe which is not connected to said charger is selected, in accordance with said detection signal.

With this configuration, when the operator removes the ultrasonic probe used for the diagnosis from the charger, only its ultrasonic probe executes the transmission and reception of the ultrasonic waves, and the ultrasonic probe that is still connected to the charger does not execute the transmission and reception of the ultrasonic waves. Thus, the ultrasonic probe connected to the charger can be charged efficiently in a short time. Also, when the operator removes the ultrasonic probe used for the diagnosis from the charger, its ultrasonic probe is automatically switched to the usable state. Thus, the operator has no necessity of storing the relation between the ultrasonic probe and the selecting switch, and there is no fear that the selecting switch is erroneously operated. Hence, the improvement of the operability can be attained, and the burden on the operator can be decreased.

According to the ultrasonic probe and charger according to the present invention, when the ultrasonic probe is connected to the charger, the transmitting and receiving operations of the ultrasonic waves can be automatically stopped, or the communication of the signal related to the transmission and reception of the transducer can be disconnected from the outside. Thus, the ultrasonic probe connected to the charger can be charged efficiently in a short time.

Also, according to the ultrasonic diagnostic apparatus and ultrasonic diagnostic system according to the present invention, when the operator removes the ultrasonic probe used for the diagnosis from the charger, only its ultrasonic probe executes the transmission and reception of the ultrasonic waves, and the ultrasonic probe that is still connected to the charger does not execute the transmission and reception of the ultrasonic waves. Thus, the ultrasonic probe connected to the charger can be charged efficiently in a short time. Also, when the operator removes the ultrasonic probe used for the diagnosis from the charger, its ultrasonic probe is automatically switched to the usable state. Thus, the operator has no necessity of memorizing the relation between the ultrasonic probe and the selecting switch, and there is no fear that the selecting switch is erroneously operated. Hence, the improvement of the operability can be attained, and the burden on the operator can be decreased.

BEST MODE FOR CARRYING OUT THE INVENTION

The present invention will be described below in detail in accordance with the preferable embodiments shown in the drawings.

<First Embodiment>

Figure 1A:
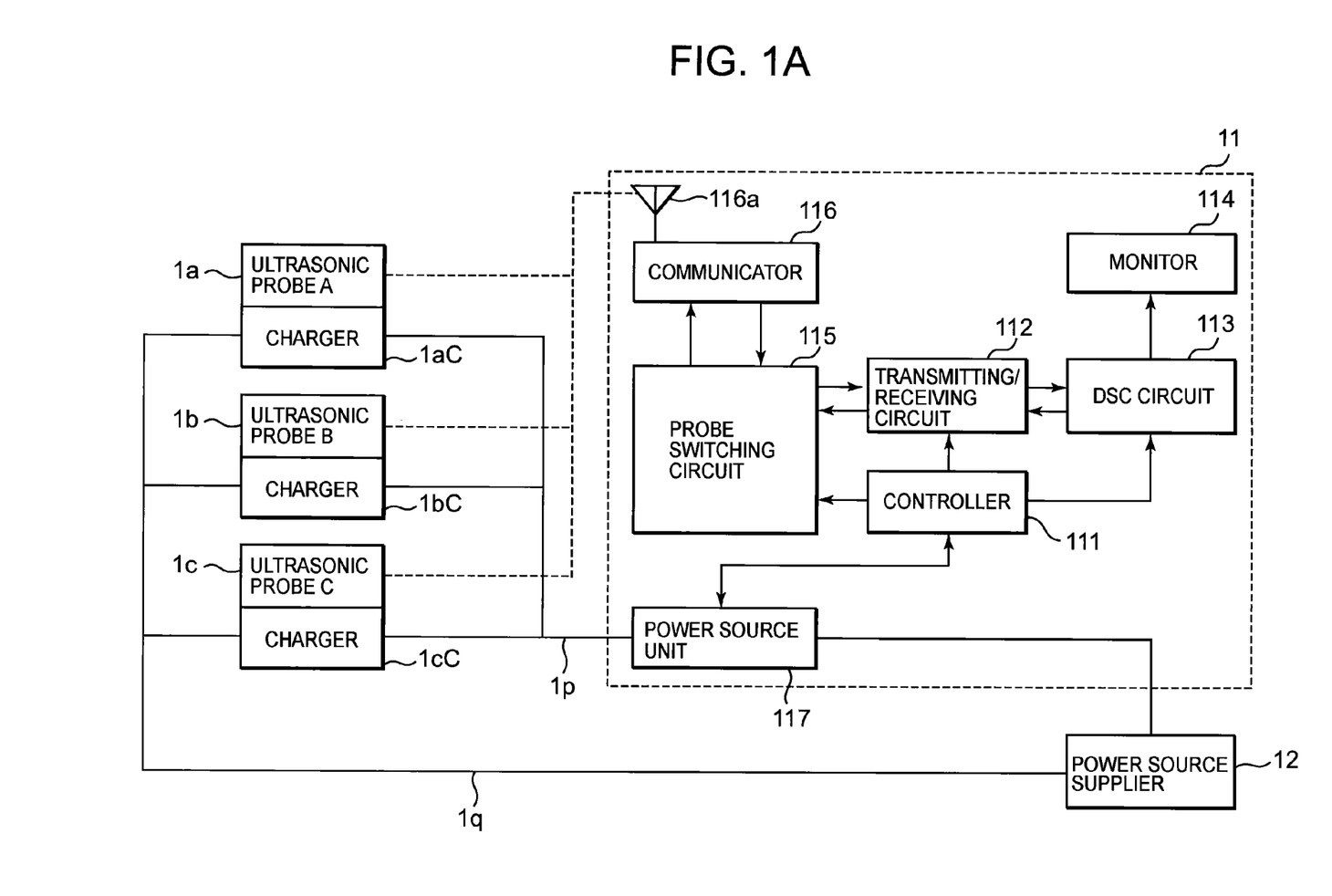
FIG. 1A is a block diagram showing a schematic configuration of a first embodiment in the ultrasonic diagnostic system according to the present invention.
Figure 1B:
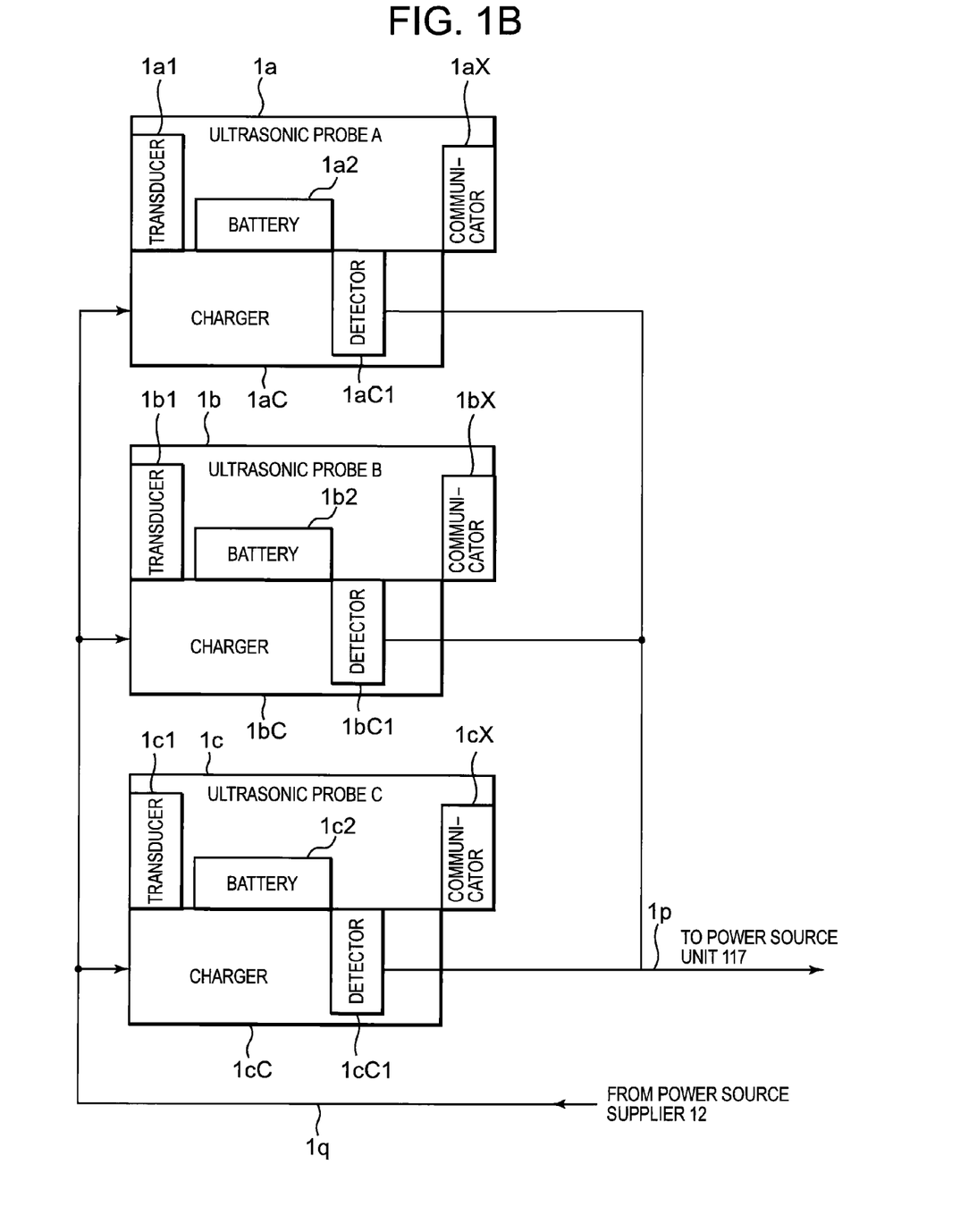
FIG. 1B is a partially detailed block diagram showing in detail a part of FIG. 1A.

FIG. 1A is a block diagram showing the schematic configuration of the first embodiment of the ultrasonic diagnostic system according to the present invention, and FIG. 1B is a partially detailed block diagram showing the detailed content of the set of the three ultrasonic probes and chargers in FIG. 1A. In FIGS. 1A and 1B, wireless (cordless) ultrasonic probes $1a$, $1b$ and $1c$ (although three ultrasonic probes are shown here, four or more ultrasonic probes may be used) for ultrasonic transmission and reception are arranged in an ultrasonic diagnostic apparatus 11 (hereafter, the ultrasonic probes $1a$, $1b$ and $1c$ are also referred to as ultrasonic probes A, B and C, respectively). The ultrasonic probes $1a$, $1b$ and $1c$ use rechargeable batteries $1a2$, $1b2$ and $1c2$ as operational power sources, respectively, and contain: transducers $1a1$, $1b1$ and $1c1$ for executing transmitting and receiving operations for the ultrasonic waves; and communicators $1aX$, $1bX$ and $1cX$ for wirelessly communicating with the outside using signals related to the transmissions and receptions by the transducers $1a1$, $1b1$ and $1c1$. By the way, each of the communicators $1aX$, $1bX$ and $1cX$ has a built-in antenna (not shown).

Here, "Signals related to Transmission and Reception" means, as for transmission, a drive control signal for mainly driving the transducer under the conditions such as a predetermined timing, a pulse width, and an aperture width and the like, and as for reception, echo signals (including an amplified signal and a converted signal such as a digitalized signal or the like) received by the transducers $1a1$, $1b1$ and $1c1$.

Those ultrasonic probes $1a$, $1b$ and $1cs$ are normally connected to chargers $1aC$, $1bC$ and $1cC$ (although three chargers are shown here, four or more chargers may be used). The chargers $1aC$, $1bC$ and $1cC$ are connected through a power source cable $1q$ to a power source supplier 12 such as a medical plug and the like. Also, the chargers $1aC$, $1bC$ and $1cC$ are configured to have detectors $1aC1$, $1bC1$ and $1cC1$ for detecting that the ultrasonic probes $1a$, $1b$ and $1c$ are connected, respectively, so that the detection signals based on the detectors $1aC1$, $1bC1$ and $1cC1$ are transmitted through a communication cable $1p$ serving as a signal transmitter to the ultrasonic diagnostic apparatus 11.

The ultrasonic diagnostic apparatus 11 contains: a controller 111 for controlling the entire apparatus; a transmitting/receiving circuit 112 that under the control of this controller 111, generates the signals related to the transmissions of the ultrasonic waves in the ultrasonic probes $1a$, $1b$ and $1c$ and generates the diagnostic information in accordance with the signals related to the receptions of the ultrasonic waves in the ultrasonic probes $1a$, $1b$ and $1c$; a DSC (Digital Scanning Converter) circuit 113 for processing various picture groups based on the diagnostic information generated by this transmitting/receiving circuit 112 and displaying on a monitor 114; a communicator 116 for executing a communication between the respective ultrasonic probes $1a$, $1b$ and $1c$; a probe switching circuit 115 for selecting any one of the ultrasonic probes $1a$, $1b$ and $1c$ and executing a switching connection so that the selected one ultrasonic probe communicates the signal related to the transmission and reception of the ultrasonic waves, through the communicator 116 to/from the transmitting/receiving circuit 112; and a power source unit 117 for receiving the electric power from the power source supplier 12 and supplying the operational electric power to the entire apparatus and also adding, to the controller 111, the connection detection signals of the ultrasonic probes 1a, 1b and 1c to the chargers 1aC, 1bC and 1cC transmitted through the communication cable 1p. By the way, the communicator 116 has an antenna 116a and executes the wireless communication between the respective communicators 1aX, 1bX and 1cX shown in FIG. 1B, as shown by the broken lines between the antenna 116a and the respective ultrasonic probes 1a, 1b and 1c, in FIG. 1A.

The operations of the first embodiment configured as mentioned above will be described below by dividing into the case in which the ultrasonic probe is not used and the case in which the ultrasonic probe is used.

<Case in which Ultrasonic Probe is not Used>

Usually, when the ultrasonic probes 1a, 1b and 1c are not used, those ultrasonic probes 1a, 1b and 1c are connected to the chargers 1aC, 1bC and 1cC, respectively. Consequently, the chargers 1aC, 1bC and 1cC receive the supply of the electric power from the power source supplier 12 and charge the batteries of the ultrasonic probes 1a, 1b and 1c. Also, when the fact that the ultrasonic probes 1a, 1b and 1c are connected to the chargers 1aC, 1bC and 1cC is detected by the detectors 1aC1, 1bC1 and 1cC1 and then its detection signal is transmitted through the communication cable 1p (the unit except the cable is allowable) to the ultrasonic diagnostic apparatus 11, its detection signal is transmitted through the power source unit 117 to the controller 111. The controller 111 has an identifying unit for recognizing that the respective ultrasonic probes 1a, 1b and 1c are connected to the chargers 1aC, 1bC and 1cC. So, when the fact that all of the ultrasonic probes 1a, 1b and 1c are connected to the chargers 1aC, 1bC and 1cC, respectively, is recognized, in such a way that the generation of the signal related to the transmission of the ultrasonic waves executed by the transmitting/receiving circuit 112 and the generation of the diagnostic information are stopped and the communications are disconnected from all of the ultrasonic probes 1a, 1b and 1c, the probe switching circuit 115 is controlled. Consequently, the ultrasonic waves are not transmitted from any of the ultrasonic probes 1a, 1b and 1c, and only the charging is performed on the respective ultrasonic probes 1a, 1b and 1c.

As a result, the ultrasonic probes 1a, 1b and 1c connected to the chargers 1aC, 1bC and 1cC, respectively, are charged efficiently in a short time, and a voltage is never applied to the transducer. Thus, a trouble that causes the deterioration in the performance of the ultrasonic probe and the reduction in the life is avoided, and the wasteful consumption of the energy is suppressed.

By the way, the above-mentioned embodiment is described for the case in which the detectors 1aC1, 1bC1 and 1cC1 are located inside the chargers 1aC, 1bC and 1cC, respectively, and the controller 111 is located inside the ultrasonic diagnostic apparatus. However, the detectors and the controller may be both located inside the ultrasonic probe.

<Case in which Ultrasonic Probe is Used>

When any one of the probes 1a, 1b and 1c connected to the chargers 1aC, 1bC and 1cC is tried to be used, the probe to be used is removed from the chargers 1aC, 1bC and 1cC. So, for example, when the probe 1a is assumed to be used, a user removes the probe 1a from the charger 1aC. Thus, its detection signal is sent from the charger 1aC through the power source unit 117 to the controller 111. Consequently, the controller 111 determines that the ultrasonic probe 1a becomes usable, and activates the transmitting/receiving circuit 112 and also controls the probe switching circuit 115 so as to communicate with the ultrasonic probe 1a. Consequently, the wireless communication is executed between the communicator 116 in the ultrasonic diagnostic apparatus 11 and the communicator 1aX in the ultrasonic probe 1a. Then, the signal related to the transmission of the ultrasonic waves is transmitted from the ultrasonic diagnostic apparatus 11 to the ultrasonic probe 1a, and the signal related to the reception of the ultrasonic waves is transmitted from the ultrasonic probe 1a to the ultrasonic diagnostic apparatus 11. At this time, the ultrasonic probe 1a transmits and receives the ultrasonic waves in accordance with the signal related to the transmission of the ultrasonic waves, and the transmitting/receiving circuit 112 generates the diagnostic information in accordance with the signal related to the reception of the ultrasonic waves. The DSC circuit 113 processes the various picture groups in accordance with the diagnostic information generated by the transmitting/receiving circuit 112 and displays on the monitor 114.

Figure 3:
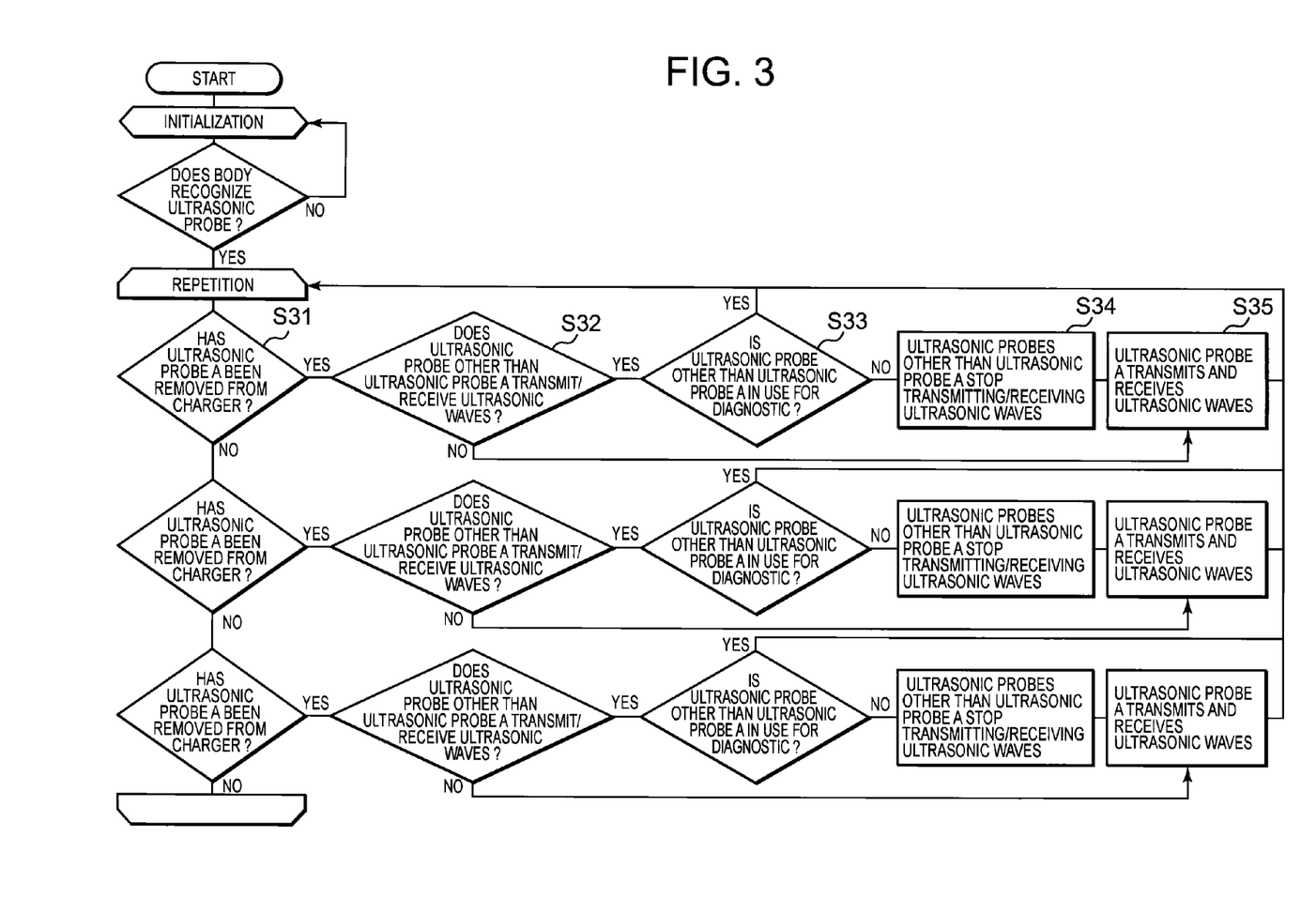
FIG. 3 is a flowchart showing one example of a probe switching procedure of the controller in the first embodiment of the present invention.

FIG. 3 is a flowchart showing one example of the probe switching procedure of the controller 111. The operations of the controller 111 will be described below in accordance with this flowchart. Here, in the controller 111 in the ultrasonic diagnostic apparatus 11, the ultrasonic probe A, the ultrasonic probe B and the ultrasonic probe C are recognized. Now, the ultrasonic probe A connected to the charger 1aC is assumed to be removed. At first, at a step S31, whether or not the ultrasonic probe A is removed from the charger 1aC is judged. Here, if it is determined as having been removed, then in step S32 determined is as to whether or not the ultrasonic probe except the ultrasonic probe A transmits and receives the ultrasonic waves. At this time, if the ultrasonic probe except the ultrasonic probe A does not transmit and receive ultrasonic waves, the ultrasonic probe A is controlled to transmit and receive ultrasonic waves in step S35. On the hand, in step S32, if it is determined that the ultrasonic probe(s) other than the ultrasonic probe A has transmitted and received ultrasonic waves, it is determined whether or not the ultrasonic probe(s) other than the ultrasonic probe A is in use for the sake of diagnosis on the basis of the change in an ultrasonic image and the like, in step S33. Here, if it is determined that the ultrasonic probe(s) other than the ultrasonic probe A is not in use, the transmission and reception of the ultrasonic waves by the ultrasonic probe(s) other than the ultrasonic probe A are stopped in step S34. Then in step S35, it is arranged that transmission and reception of the ultrasonic waves by the ultrasonic probe A are possible, and the operational flow returns to the process of step S31. In this way, in the course of repeating the processes in steps S31 to S35, for example, if it is determined that the ultrasonic probe(s) other than the ultrasonic probe A is in use for the sake of diagnosis in step S33, the original determination that the ultrasonic probe A has been removed is considered to be caused by a false operation, and the transmission and reception situations of the ultrasonic waves are designed to be unchanged.

In the above, described is the probe switching procedure when the ultrasonic probe A has been removed from the charger 1aC. However, when the ultrasonic probes B or C other than the above has been removed from the chargers 1bC, 1cC, respectively, the switching operation is executed in accordance with the procedure similar to the procedure shown in FIG. 3. By the way, the switching procedure of the ultrasonic probe shown here is one example, and the switching procedure of the ultrasonic probe of the present invention is not limited thereto.

Also, in the first embodiment, it is needless to say that as the detectors 1aC1, 1bC1 and 1cC1 for detecting that the ultrasonic probes 1a, 1b and 1c are connected to the chargers 1aC, 1bC and 1cC respectively may be used various known devices. For example, a magnetic device such as an IC tag, or a device for identifying by optically reading like a bar code or an infrared sensor may be used. Furthermore, detection based on a mechanical switch that is actuated when the ultrasonic probes 1a, 1b and 1c are connected to the chargers 1aC, 1bC and 1cC, or identification based on an electrical contact between the terminals mounted on the ultrasonic probes 1a, 1b and 1c and the terminals mounted on the chargers 1aC, 1bC and 1cC may be used.

The first embodiment is configured such that the detectors 1aC1, 1bC1 and 1cC1 for detecting that the ultrasonic probes 1a, 1b and 1c are connected to the chargers 1aC, 1bC and 1cC, respectively, are arranged on the sides of the chargers 1aC, 1bC and 1cC as shown in FIG. 1B and its detection signal is transmitted through the communication cable 1p to the ultrasonic diagnostic apparatus 11. However, the present invention is not limited to such configuration. That is, the detectors for detecting that the ultrasonic probes 1a, 1b and 1c are connected to the chargers 1aC, 1bC and 1cC, respectively, may be arranged on the sides of the ultrasonic probes 1a, 1b and 1c, or may be arranged on both the sides of the ultrasonic probes 1a, 1b and 1c and the chargers 1aC, 1bC and 1cC. However, when the detectors are arranged on the sides of the ultrasonic probes 1a, 1b and 1c, the detection signal in the connection state can be wirelessly transmitted from the communicators 1aX, 1bX and 1cX of the cordless ultrasonic probes to the ultrasonic diagnostic apparatus 11. In this case, the ultrasonic diagnostic apparatus body side can control so as to prevent the probe from transmitting the ultrasonic waves. Even in case that the detectors are arranged on the side of the chargers 1aC, 1bC and 1cC, the detection signal may be wirelessly transmitted to the ultrasonic diagnostic apparatus 11.

In the above-mentioned first embodiment, in the case that the ultrasonic probes 1a, 1b and 1c have been connected to the chargers 1aC, 1bC and 1cC, respectively, the controller 111 in the ultrasonic diagnostic apparatus 11 controls the probe switching circuit 115 so that the transmitting and receiving operations of the ultrasonic waves executed by the respective transducers in the ultrasonic probes 1a, 1b and 1c are stopped. However, in the case that the ultrasonic probes 1a, 1b and 1c have the detectors for detecting the fact that they are connected to the chargers 1aC, 1bC and 1cC for charging the batteries, respectively, the controllers for stopping the transmitting and receiving operations of the ultrasonic waves executed by the transducers can also be arranged in the ultrasonic probes 1a, 1b and 1c themselves. In the case that the sides of the chargers 1aC, 1bC and 1cC contain the detectors for detecting the connections of the ultrasonic probes 1a, 1b and 1c, respectively, the controllers for stopping the transmitting and receiving operations of the ultrasonic waves executed by the transducers can be similarly arranged in the chargers 1aC, 1bC and 1cC. Consequently, it is possible to surely prevent the ultrasonic probe, which is in process of charging, from transmitting and receiving the ultrasonic waves.

In this case, inside the controller 111 in FIG. 1A, the functional portions that respond to the detection signals from the detectors may be arranged on the sides of the ultrasonic probes 1a, 1b and 1c in which the detectors are arranged and/or in the chargers 1aC, 1bC and 1cC.

Figure 1C:
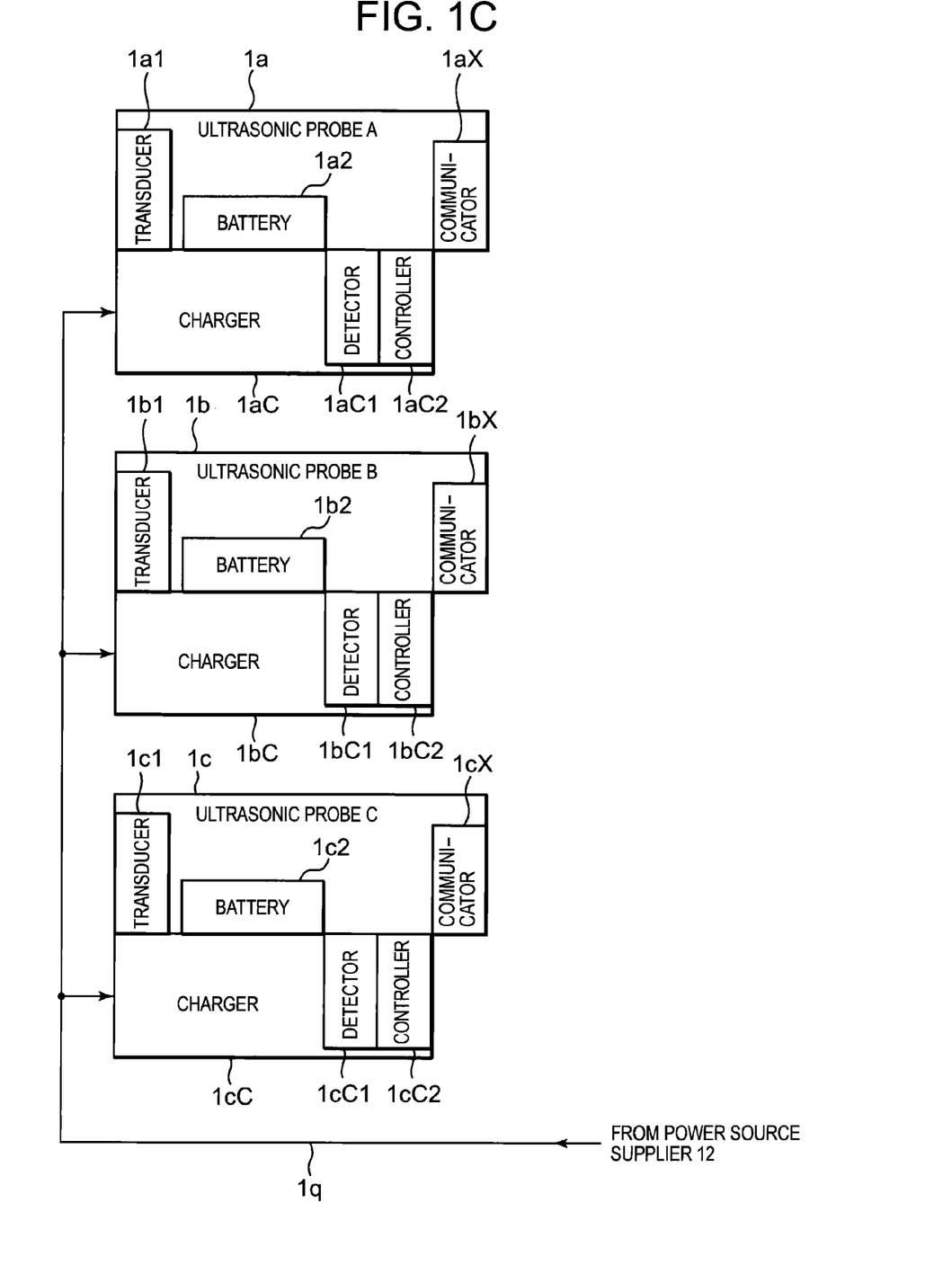
FIG. 1C is a partially detailed block diagram showing a first variation of the first embodiment shown in FIG. 1A, similarly to FIG. 1A.

FIG. 1C is a view showing a part of the first variation of the first embodiment in a manner similar to FIG. 1A. FIG. 1C shows a case in which the detectors 1aC1, 1bC1 and 1cC1 are arranged in the chargers 1aC, 1bC and 1cC, respectively, and controllers 1aC2, 1bC2 and 1cC2 responding to the detection signals from the detectors 1aC1, 1bC1 and 1cC1 are arranged in the chargers 1aC, 1bC and 1cC. The respective controllers 1aC2, 1bC2 and 1cC2 have built-in communicators (not shown), and those communicators can communicate with the communicators 1aX, 1bX and 1cX in the respective corresponding ultrasonic probes 1a, 1b and 1c. That is, in the embodiment of FIGS. 1A and 1B, the detection signals in the communicators 1aX, 1bX and 1cX are transmitted through the communication cable 1p to the ultrasonic diagnostic apparatus 11 and to be recognized by the controller 111 in the ultrasonic diagnostic apparatus 11, and the control of the transmission and reception of the ultrasonic waves is executed between the communicator 116 in the ultrasonic diagnostic apparatus 11 and the communicators 1aX, 1bX and 1cX in the corresponding ultrasonic probes 1a, 1b and 1c. However, in the first variation shown in FIG. 1C, in accordance with the identification results in the respective controllers 1aC2, 1bC2 and 1cC2, the control of the transmission and reception of the ultrasonic waves is executed through the communication between the built-in communicators in the controllers 1aC2, 1bC2 and 1cC2 and the communicators 1aX, 1bX and 1cX in the corresponding ultrasonic probes 1a, 1b and 1c.

Figure 1D:
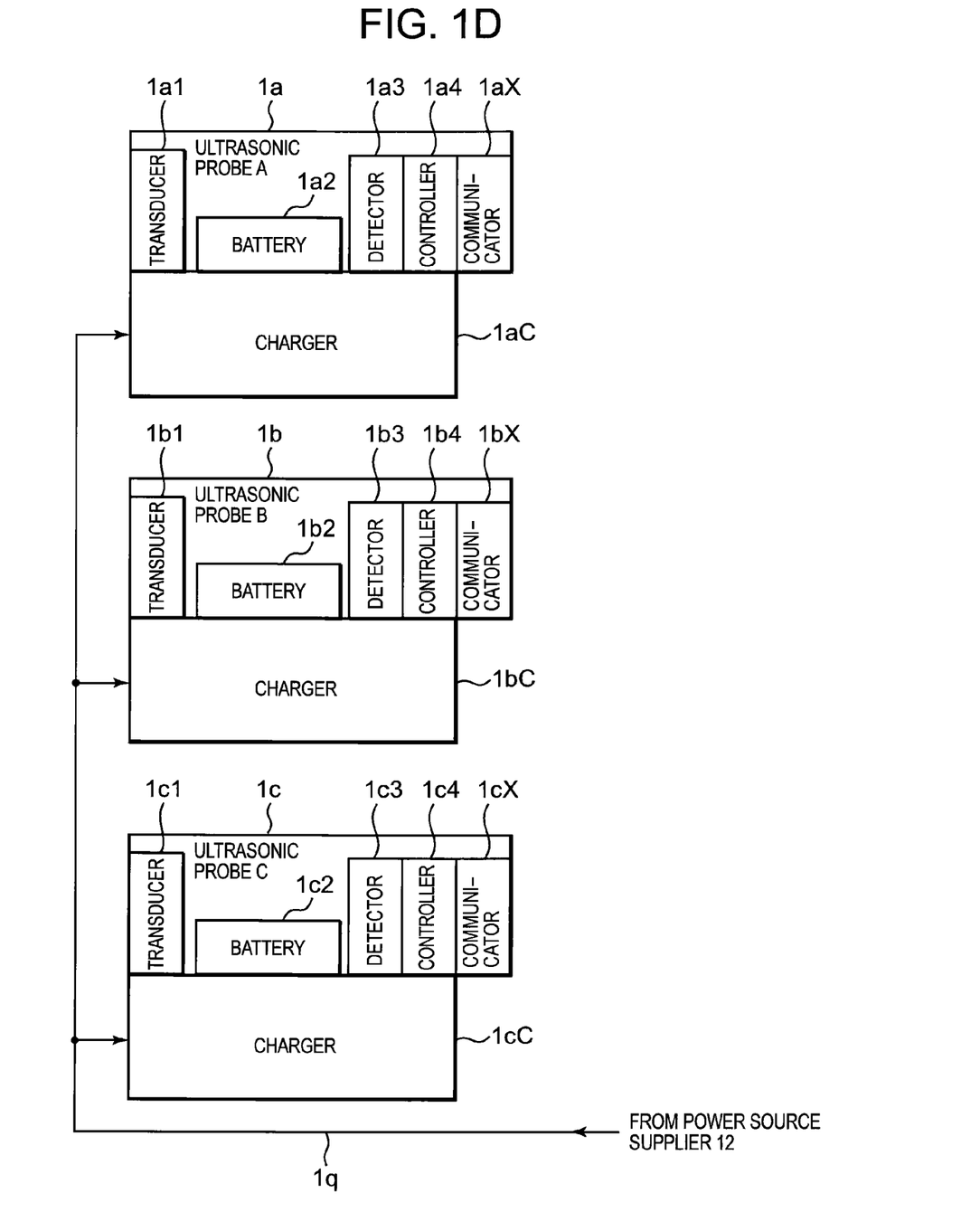
FIG. 1D is a partially detailed block diagram showing a second variation of the first embodiment shown in FIG. 1A, similarly to FIG. 1A.

FIG. 1D is a view showing a part of a second variation of the first embodiment, in a manner similar to FIG. 1A. That is, FIG. 1D shows a case in which detectors 1a3, 1b3 and 1c3 are arranged in the ultrasonic probes 1a, 1b and 1c, respectively, and controllers 1a4, 1b4 and 1c4 corresponding to the detection signals from the detectors 1a3, 1b3 and 1c3 are also arranged in the ultrasonic probes 1a, 1b and 1c. In the second variation shown in FIG. 1D, in accordance with the identification results in the respective controllers 1a4, 1b4 and 1c4, the controls of the transmissions and receptions of the ultrasonic waves in the respective corresponding ultrasonic probes 1a, 1b and 1c are executed.

<Second Embodiment>

Figure 2:
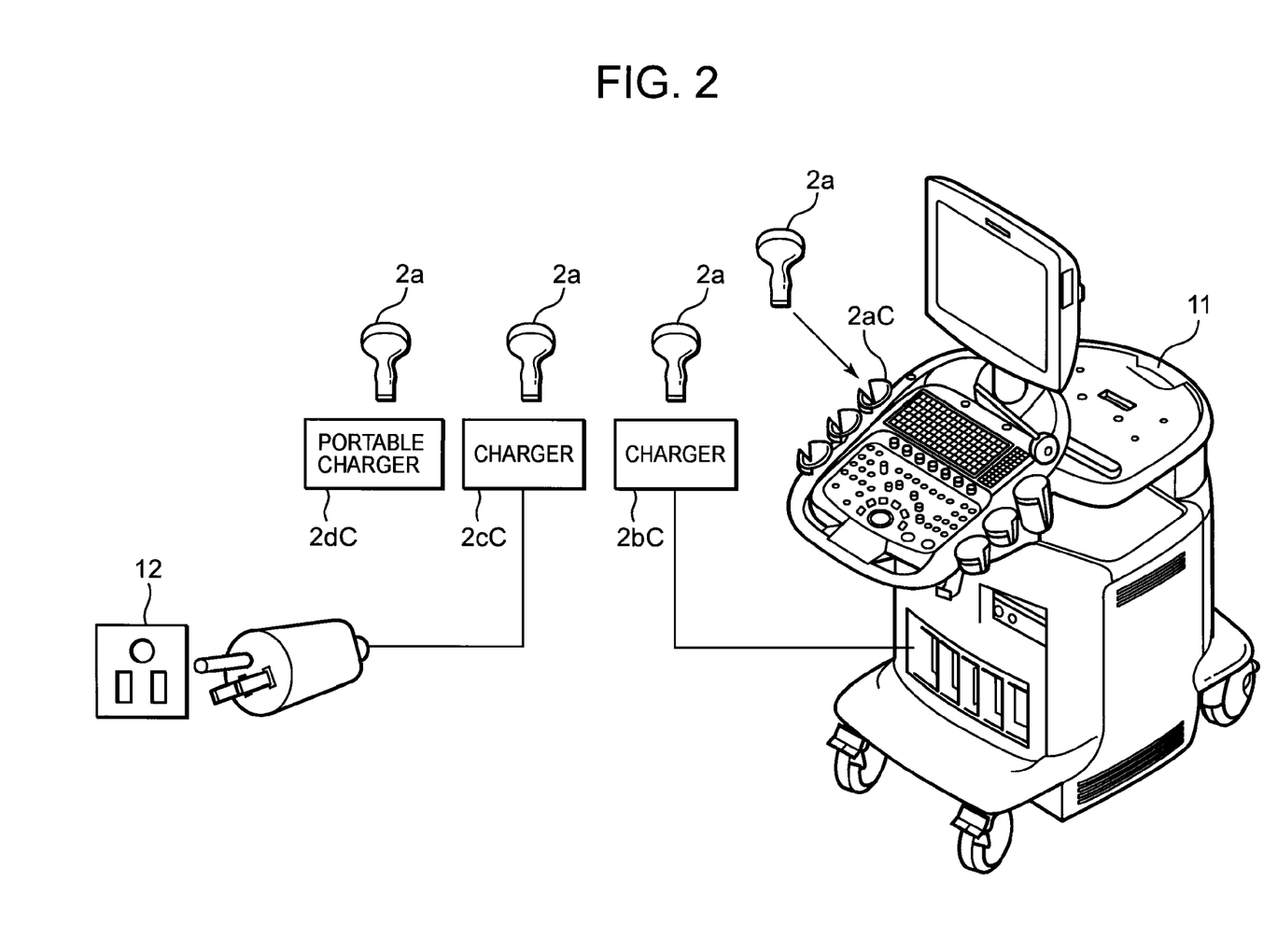
FIG. 2 is a perspective view showing a schematic configuration of a second embodiment in the ultrasonic diagnostic system according to the present invention.

FIG. 2 is a perspective view showing the schematic configuration of the second embodiment of the ultrasonic diagnostic system according to the present invention, and exemplifies a case in which as compared with the ultrasonic diagnostic apparatus 11 shown in FIG. 1A, four wireless ultrasonic probes 2a are arranged as essential elements, and those ultrasonic probes 2a are connected to chargers 2aC, 2bC, 2cC and 2dC whose configurations differ from each other. So, the respective chargers 2aC, 2bC, 2cC and 2dC will be described below.

The charger 2aC is shown as a component integrated with the ultrasonic diagnostic apparatus 11. For example, the component in which the function of the charger is added to a probe holder is considered. The charger 2bC is shown as a component that is connected to the power source unit 117 (see FIG. 1A) in the ultrasonic diagnostic apparatus 11 by using a cable and the like is shown. This configuration eliminates the necessity of arranging the charger 2bC in the vicinity of the ultrasonic diagnostic apparatus 11. For example, the charger 2bC can be placed and used in the vicinity of an examinee (patient). It is shown that for the charger 2cC the supply of the power source is performed from the external power source supplier 12 (the medical plug and the like). Since this configuration eliminates the constraint that the ultrasonic diagnostic apparatus 11 supplies the power source to the ultrasonic probe 2a, there is no fear of the supply lack with regard to the capacity of the power source. Also, in the ultrasonic probe 2a, the charging is possible at any position where the power source supplier 12 exists. Thus, there is no necessity of arranging the charger 2cC in the vicinity of the ultrasonic diagnostic apparatus 11, and there is also a convenience that, even when the power source of the ultrasonic diagnostic apparatus 11 is in off state, the battery of the ultrasonic probe 2a can be charged. The charger 2dC is shown as one arranged as of a portable type. Consequently, the charging of the battery in the ultrasonic probe 2a can be performed any where at any time. Hence, even in an emergent case or under an environment in which the power source supplier 12 such as the medical plug or the like does not exist, the battery of the ultrasonic probe 2a can be charged.

Figure 4A:
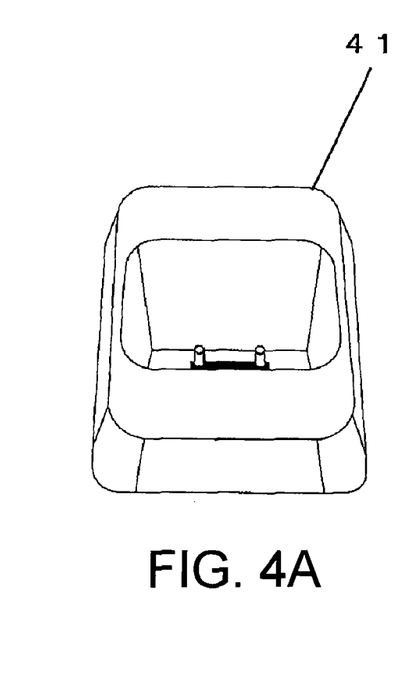
FIGS. 4A, 4B, 4C and 4D are views showing the shape examples of the chargers in the first and second embodiments of the present invention.
Figure 4B:
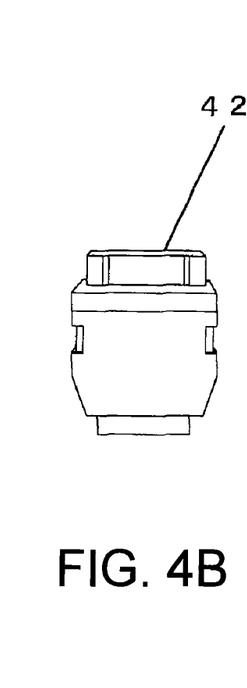
Figure 4C:
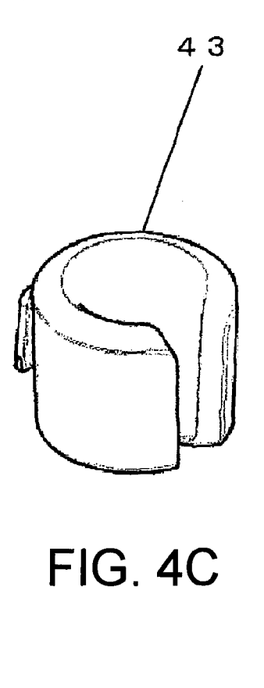
Figure 4D:
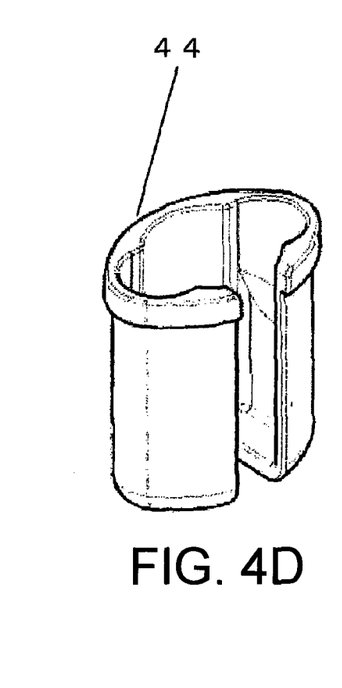

FIGS. 4A to 4D are views showing the shape examples of the chargers in the above-mentioned respective embodiments. Among them, a charger 41 shown in FIG. 4A indicates, for example, the shape such as a desktop holder of a portable telephone, and the ultrasonic probe is connected thereto. A charger 42 shown in FIG. 4B indicates, for example, a shape such as a connection connector used to charge the portable telephone or the other electric equipment, and this connection connector is connected to the ultrasonic probe. A charger 43 shown in FIG. 4C and a charger 44 shown in FIG. 4D are those where, for example, the function of a charger is added to the probe holder. By the way, the shape examples of the chargers shown here indicate one example, and they do not evidently define the shape of the charger according to the present invention.

Figure 5:
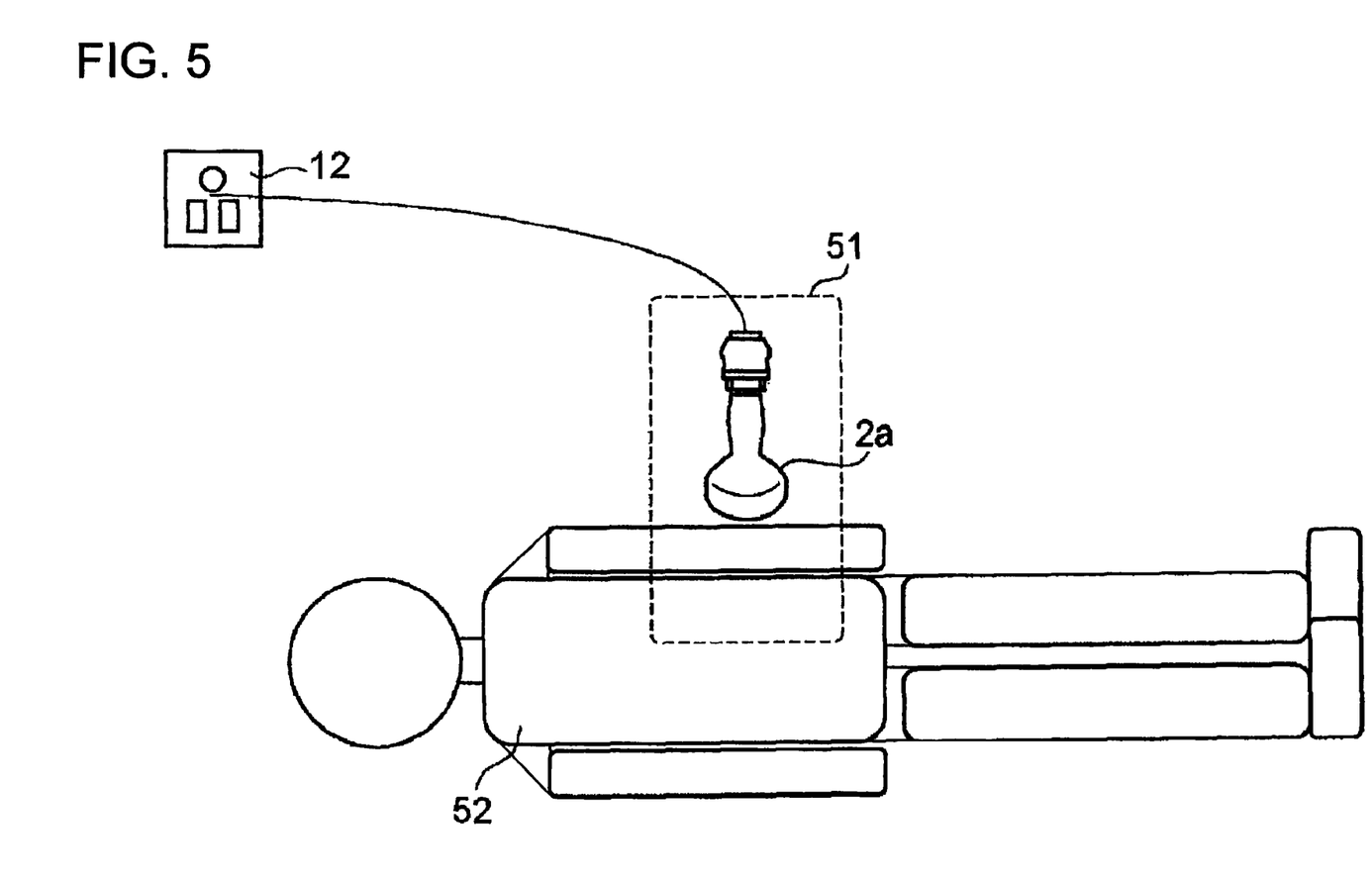
FIG. 5 is a view showing an example in which, by using one charger in the second embodiment of the present invention, the diagnosis is executed while the charging is executed.

Now an example will be described hereinbelow using FIG. 5, wherein diagnosis is performed during charging by way of a charger according to the second embodiment of the present invention. Unless charging has been performed in the cordless ultrasonic probe that is operated with a chargeable battery as the power source, the ultrasonic probe cannot be used. For this reason, when the ultrasonic probe is not used for diagnosis, it is assumed that the ultrasonic probe has been connected to the charger. However, it can also be assumed that the user may forget to connect the ultrasonic probe to the charger. When it is desired to emergently use an ultrasonic diagnostic apparatus, it would be very inconvenient if it is necessary to wait for battery charging. So, as shown in FIG. 5, an ultrasonic probe 51 that remains connected to the charger is used, and the stopping of the transmitting and receiving operations of the ultrasonic waves is released, and ultrasonic diagnosis of an examinee 52 may be consequently executed. At that time, under the consideration of the safety to the examinee 52, floating is naturally required to be executed between the external power source supplier 12 (the medical plug or the like) and a probe 21, by using a transformer or the like.

Figure 6A:
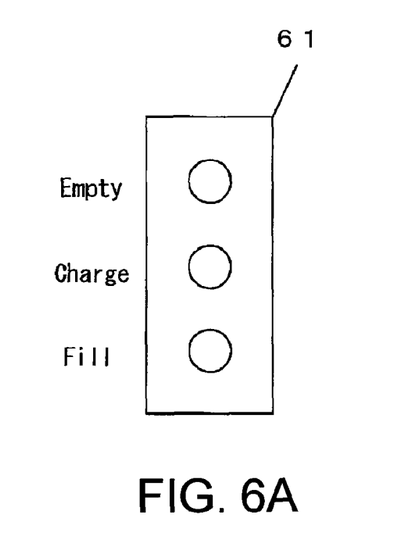
FIGS. 6A, 6B are schematic configuration views of a display for displaying the charged state of the ultrasonic probe in the first and second embodiments of the present invention.
Figure 6B:
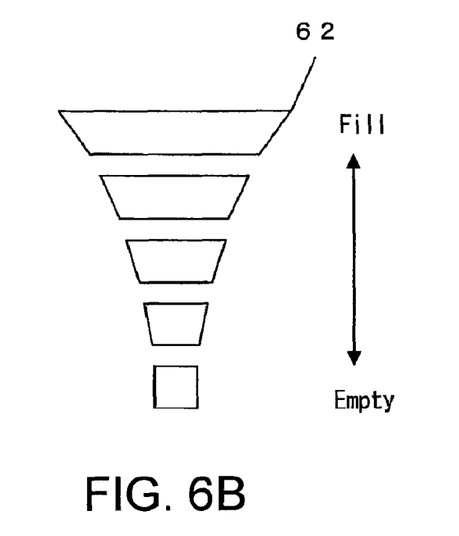

FIGS. 6A and 6B are schematic configuration views of charging state displays for displaying the charging state of the ultrasonic probes in the above-mentioned embodiments. In the above views, in a charging state display 61 shown in FIG. 6A, LEDs, whose color varies correspondingly to a filled state (Fill), a charging state (Charge) and an empty state (Empty), are arranged, and in a charging state display 62 shown in FIG. 6B, a plurality of light emitting devices whose lateral widths are sequentially different from the empty state (Empty) to the filled state (Fill). The charging state display 61 or 62 may be arranged on the ultrasonic probe itself or the charger. Consequently, since the charging state of the ultrasonic probe can be identified at a glance, the oblivion of charging is protected. By the way, the shape of the display shown here indicates one example, and the shape of the display according to the present invention is not evidently limited thereto.

<Third Embodiment>

Figure 7:
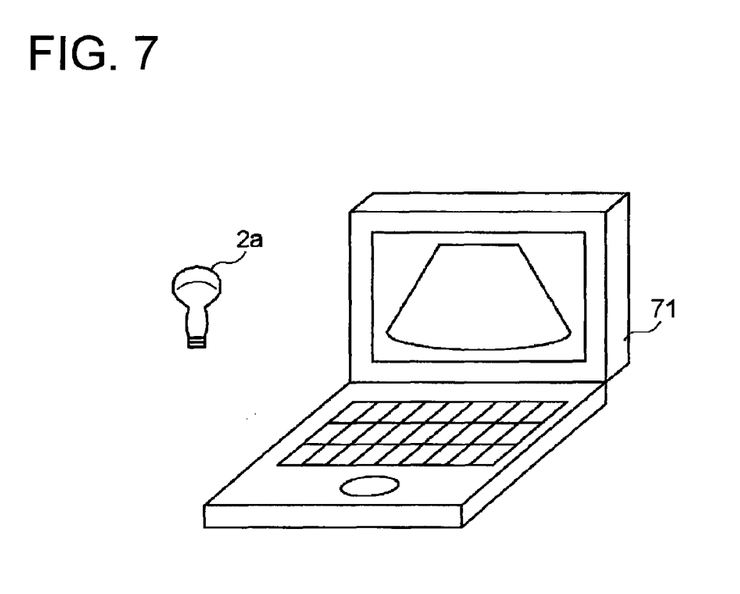
FIG. 7 is a perspective view showing a schematic configuration in a third embodiment of the ultrasonic diagnostic system according to the present invention.

FIG. 7 is a perspective view showing the schematic configuration of the third embodiment in the ultrasonic diagnostic system according to the present invention. For example, a portable ultrasonic diagnostic apparatus 71 such as a notebook personal computer is used. Since the portable ultrasonic diagnostic apparatus 71 shown in FIG. 7 is small in size, it is difficult to reserve a position at which a conventional probe connector is to be mounted, and there is a limit of the size of the battery. For this reason, as the ultrasonic probe combined with the portable ultrasonic diagnostic apparatus 71, the development of the wireless ultrasonic probe 2a in which the battery of the charging type is built is requested. As this portable ultrasonic diagnostic apparatus 71 and the wireless ultrasonic probe 2a become popular, the use region of the ultrasonic diagnosis may extend more and more, without regard to inside or outside a hospital or the like. This third embodiment is very effective when the use in such occasion is considered.

Figure 8:
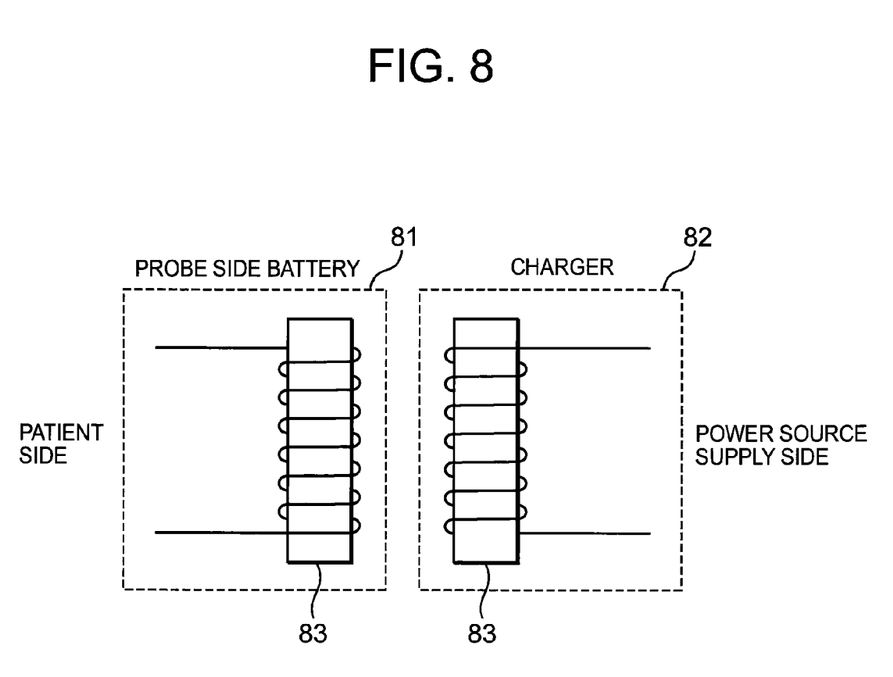
FIG. 8 is a description view describing one example of a charging method of the ultrasonic probe in the second embodiment of the present invention.

FIG. 8 is a descriptive view for describing one example of the charging method of the ultrasonic probe. As described by using FIG. 5, when the diagnosis is executed while the ultrasonic probe is charged by the charger, by using the insulating transformer between the examinee and the external power source supplier (the medical plug or the like), the patient side is required to be floated from the power source supply side. FIG. 8 shows its configuration example, and between a probe side battery 81 that is on the patient side and a power source side charger 81, it is desired that insulating transformers 83 insulated from each other are used to supply the electric power. This configuration increases the safety. By the way, FIG. 8 shows only a part of the probe side battery 81 and the power source side charger 82.

According to the ultrasonic probe and the charger according to the present invention, when they are not used, the transmission of the ultrasonic waves is stopped, which can protect the deterioration in the performance of the probe and the reduction in the life, and can suppress the wasteful energy consumption and contribute to the energy saving. Thus, they are useful for establishing the ultrasonic diagnostic system.

Also, according to the ultrasonic diagnostic apparatus and ultrasonic diagnostic system according to the present invention, when the user selects the probe corresponding to the diagnosis target from the plurality of probes, the probe to be used is removed from the charger. Thus, since the removed probe is automatically switched to the usable state, the user has no necessity of memorizing the correspondence relation between the probe and the selecting switch, and there is no fear that the selecting switch is erroneously operated. Hence, the operability is very improved, and the burden on the user is decreased, which is useful for the ultrasonic diagnostic system.

The invention claimed is:

1. An ultrasonic diagnostic apparatus that uses respective rechargeable batteries as operational power sources, and sets, as the target of a communication, a plurality of ultrasonic probes for executing: a transmission and a reception of ultrasonic waves to and from an examinee; and a wireless transmission/reception of signals related to the transmission and the reception of said ultrasonic waves, to and from an external apparatus, and selects any one of said plurality of ultrasonic probes, in accordance with detection signals obtained by detecting that said ultrasonic probes are connected to respective chargers for charging said batteries, and transmits/receives the signals related to the transmission and the reception of said ultrasonic waves, the ultrasonic diagnostic apparatus comprising:

a wireless communicator, configured to wirelessly communicate the signals related to the transmission and the reception of said ultrasonic waves;

a transmitting and receiving circuit for generating a signal related to the transmission of an ultrasonic signal in an ultrasonic probe, and supplying it to said wireless communicator as the transmission signal to said ultrasonic probe, and generating a diagnostic information on the basis of the signals related to the reception of the ultrasonic waves in said ultrasonic probe that is received in said wireless communicator;
a probe switching circuit for selecting any one of said plurality of ultrasonic probes and enabling the transmission/reception to/from said transmitting and receiving circuit; and
a controller configured to control said probe switching circuit so that said ultrasonic probe which is not connected to said charger is selected, in accordance with said detection signal, and to determine whether another ultrasonic probe, of the plurality of ultrasonic probes, that is currently transmitting and receiving further ultrasonic waves is also currently in use for diagnosis from a change in an ultrasonic image, and to stop the transmitting and the receiving of the further ultrasonic waves by the another ultrasonic probe when it is not currently in use for diagnosis.

2. The ultrasonic diagnostic apparatus of claim 1, wherein each one of said respective chargers being connected to an external power source separately provided from said ultrasonic diagnostic apparatus, each one of said respective chargers being separate from the ultrasonic diagnostic apparatus and being arranged to receive charging power for charging said batteries from said power source.

3. An ultrasonic diagnostic system comprising: a plurality of ultrasonic probes for transmitting and receiving ultrasonic waves, a plurality of chargers for charging said ultrasonic probes respectively and individually, and an ultrasonic diagnostic apparatus for transmitting/receiving a signal to/from said ultrasonic probes to generate diagnostic information, wherein
each one of said plurality if ultrasonic probes comprises:
a rechargeable battery;
a transducer that uses said battery as an operational power source and transmits and receives ultrasonic waves to and from an examinee; and
a first wireless communicator operatively connected to said battery to use said battery as an operational power source and configured to wirelessly communicate, using a signal related to the transmission and reception of said transducer, with said ultrasonic diagnostic apparatus,
each one of said plurality of chargers comprises:
a detector for detecting that an ultrasonic probe of said plurality of ultrasonic probes is connected; and
a signal transmitter circuit configured to transmit a detection signal from said detector to said ultrasonic diagnostic apparatus, and
said ultrasonic diagnostic apparatus comprises:
a wireless communicator, configured to wirelessly communicate by using a signal related to the transmission and reception of said ultrasonic waves;
a transmitting and receiving circuit for generating the signal related to the transmission of the ultrasonic waves by said ultrasonic probe, and supplying it to said wireless communicator as a transmission signal to said ultrasonic probe, and generating diagnostic information in accordance with the signal related to the reception of the ultrasonic waves in said ultrasonic probe, which signal is received by said wireless communicator;
a probe switching circuit for selecting any one of said plurality of ultrasonic probes to enable the transmission/reception to/from said transmitting and receiving circuit; and
a controller configured to control said probe switching circuit so that said ultrasonic probe which is not connected to said charger is selected, in accordance with said detection signal, and to determine whether another ultrasonic probe, of the plurality of ultrasonic probes, that is currently transmitting and receiving further ultrasonic waves is also currently in use for diagnosis from a change in an ultrasonic image, and to stop the transmitting and the receiving of the further ultrasonic waves by the another ultrasonic probe when the another ultrasonic probe is determined not to be currently in use for diagnosis.

4. The ultrasonic diagnostic system of claim 3, wherein each one of said plurality of chargers being connected to an external power source separately provided from said ultrasonic diagnostic apparatus, each one of said plurality of chargers being separate from the ultrasonic diagnostic apparatus and being arranged to receive charging power for charging said batteries from said power source.

5. An ultrasonic diagnostic apparatus that uses respective rechargeable batteries as operational power sources, and sets, as the target of a communication, a plurality of ultrasonic probes for executing: a transmission and a reception of ultrasonic waves to and from an examinee; and a wireless transmission/reception of signals related to the transmission and the reception of said ultrasonic waves, to and from an external apparatus, and selects any one of said plurality of ultrasonic probes, in accordance with detection signals obtained by detecting that said ultrasonic probes are connected to respective chargers for charging said batteries, and transmits/receives the signals related to the transmission and the reception of said ultrasonic waves, the ultrasonic diagnostic apparatus comprising:
a wireless communicator, configured to wirelessly communicate the signals related to the transmission and the reception of said ultrasonic waves;
a transmitting and receiving circuit for generating a signal related to the transmission of an ultrasonic signal in an ultrasonic probe, and supplying it to said wireless communicator as the transmission signal to said ultrasonic probe, and generating a diagnostic information on the basis of the signals related to the reception of the ultrasonic waves in said ultrasonic probe that is received in said wireless communicator;
a probe switching circuit for selecting any one of said plurality of ultrasonic probes and enabling the transmission/reception to/from said transmitting and receiving circuit; and
a controller configured to control said probe switching circuit so that said ultrasonic probe which is not connected to said charger is selected, in accordance with said detection signal, and to determine whether another ultrasonic probe, of the plurality of ultrasonic probes, that is currently transmitting and receiving further ultrasonic waves is also currently in use for diagnosis from one of a change in an ultrasonic image and a change in echo signals forming an ultrasonic image as well as amplified and/or digitized signals all resulted from the echo signals, and to stop the transmitting and the receiving of the further ultrasonic waves by the another ultrasonic probe when it is not currently in use for diagnosis.

6. An ultrasonic diagnostic system comprising: a plurality of ultrasonic probes for transmitting and receiving ultrasonic waves, a plurality of chargers for charging said ultrasonic probes respectively and individually, and an ultrasonic diagnostic apparatus for transmitting/receiving a signal to/from said ultrasonic probes to generate diagnostic information, wherein each one of said plurality if ultrasonic probes comprises:
a rechargeable battery;
a transducer that uses said battery as an operational power source and transmits and receives ultrasonic waves to and from an examinee; and
a first wireless communicator operatively connected to said battery to use said battery as an operational power source and configured to wirelessly communicate, using a signal related to each one of said plurality of chargers comprises:
a detector for detecting that an ultrasonic probe of said plurality of ultrasonic probes is connected; and
a signal transmitter circuit configured to transmit a detection signal from said detector to said ultrasonic diagnostic apparatus, and said ultrasonic diagnostic apparatus comprises:
a wireless communicator, configured to wirelessly communicate by using a signal related to the transmission and reception of said ultrasonic waves;
a transmitting and receiving circuit for generating the signal related to the transmission of the ultrasonic waves by said ultrasonic probe, and supplying it to said wireless communicator as a transmission signal to said ultrasonic probe, and generating diagnostic information in accordance with the signal related to the reception of the ultrasonic waves in said ultrasonic probe, which signal is received by said wireless communicator;
a probe switching circuit for selecting any one of said plurality of ultrasonic probes to enable the transmission/reception to/from said transmitting and receiving circuit; and
a controller configured to control said probe switching circuit so that said ultrasonic probe which is not connected to said charger is selected, in accordance with said detection signal, and to determine whether another ultrasonic probe, of the plurality of ultrasonic probes, that is currently transmitting and receiving further ultrasonic waves is also currently in use for diagnosis from one of a change in an ultrasonic image and a change in echo signals forming an ultrasonic image as well as amplified and/or digitized signals all resulted from the echo signals, and to stop the transmitting and the receiving of the further ultrasonic waves by the another ultrasonic probe when the another ultrasonic probe is determined not to be currently in use for diagnosis.

7. An ultrasonic diagnostic apparatus that uses respective rechargeable batteries as operational power sources, and sets, as the target of a communication, a plurality of ultrasonic probes for executing: a transmission and a reception of ultrasonic waves to and from an examinee; and a wireless transmission/reception of signals related to the transmission and the reception of said ultrasonic waves, to and from an external apparatus, and selects any one of said plurality of ultrasonic probes, in accordance with detection signals obtained by detecting that said ultrasonic probes are connected to respective chargers for charging said batteries, each one of said respective chargers being connected to an external power source separately provided from said ultrasonic diagnostic apparatus, each one of said respective chargers being separate from the ultrasonic diagnostic apparatus and being arranged to receive charging power for charging said batteries from said power source, and transmits/receives the signals related to the transmission and the reception of said ultrasonic waves, the ultrasonic diagnostic apparatus comprising:

a wireless communicator, configured to wirelessly communicate the signals related to the transmission and the reception of said ultrasonic waves;
a transmitting and receiving circuit for generating a signal related to the transmission of an ultrasonic signal in an ultrasonic probe, and supplying it to said wireless communicator as the transmission signal to said ultrasonic probe, and generating a diagnostic information on the basis of the signals related to the reception of the ultrasonic waves in said ultrasonic probe that is received in said wireless communicator;
a probe switching circuit for selecting any one of said plurality of ultrasonic probes and enabling the transmission/reception to/from said transmitting and receiving circuit; and
a controller configured to control said probe switching circuit so that said ultrasonic probe which is not connected to said charger is selected, in accordance with said detection signal, and to determine whether another ultrasonic probe, of the plurality of ultrasonic probes, that is currently transmitting and receiving further ultrasonic waves is also currently in use for diagnosis from one of a change in an ultrasonic image and a change in echo signals forming an ultrasonic image as well as amplified and/or digitized signals all resulted from the echo signals, and to stop the transmitting and the receiving of the further ultrasonic waves by the another ultrasonic probe when it is not currently in use for diagnosis.

8. An ultrasonic diagnostic system comprising: a plurality of ultrasonic probes for transmitting and receiving ultrasonic waves, a plurality of chargers for charging said ultrasonic probes respectively and individually, and an ultrasonic diagnostic apparatus for transmitting/receiving a signal to/from said ultrasonic probes to generate diagnostic information, each one of said plurality of chargers being connected to an external power source separately provided from said ultrasonic diagnostic apparatus, each one of said plurality of chargers being separate from the ultrasonic diagnostic apparatus and being arranged to receive charging power for charging said batteries from said power source, wherein each one of said plurality if ultrasonic probes comprises:
a rechargeable battery;
a transducer that uses said battery as an operational power source and transmits and receives ultrasonic waves to and from an examinee; and
a first wireless communicator operatively connected to said battery to use said battery as an operational power source and configured to wirelessly communicate, using a signal related to the transmission and reception of said transducer, with said ultrasonic diagnostic apparatus, each one of said plurality of chargers comprises:
a detector for detecting that an ultrasonic probe of said plurality of ultrasonic probes is connected; and
a signal transmitter circuit configured to transmit a detection signal from said detector to said ultrasonic diagnostic apparatus, and said ultrasonic diagnostic apparatus comprises:
a wireless communicator, configured to wirelessly communicate by using a signal related to the transmission and reception of said ultrasonic waves;
a transmitting and receiving circuit for generating the signal related to the transmission of the ultrasonic waves by said ultrasonic probe, and supplying it to said wireless communicator as a transmission signal to said ultrasonic probe, and generating diagnostic information in accordance with the signal related to the reception of the ultrasonic waves in said ultrasonic probe, which signal is received by said wireless communicator;

a probe switching circuit for selecting any one of said plurality of ultrasonic probes to enable the transmission/reception to/from said transmitting and receiving circuit; and a controller configured to control said probe switching circuit so that said ultrasonic probe which is not connected to said charger is selected, in accordance with said detection signal, and to determine whether another ultrasonic probe, of the plurality of ultrasonic probes, that is currently transmitting and receiving further ultrasonic waves is also currently in use for diagnosis from one of a change in an ultrasonic image and a change in echo signals forming an ultrasonic image as well as amplified and/or digitized signals all resulted from the echo signals, and to stop the transmitting and the receiving of the further ultrasonic waves by the another ultrasonic probe when the another ultrasonic probe is determined not to be currently in use for diagnosis.

\* \* \* \* \*